United States Patent [19]

Doorakian et al.

[11] 4,329,480
[45] May 11, 1982

[54] CYCLIC META-SULFONIUM-PHENOXIDE ZWITTERIONS

[75] Inventors: George A. Doorakian, Waltham, Mass.; Donald L. Schmidt, Midland, Mich.

[73] Assignee: The Dow Chemical Company, Midland, Mich.

[21] Appl. No.: 253,477

[22] Filed: Apr. 13, 1981

Related U.S. Application Data

[63] Continuation of Ser. No. 892,049, Mar. 31, 1978, abandoned, which is a continuation of Ser. No. 582,554, May 29, 1975, abandoned.

[51] Int. Cl.³ .................... C07D 333/16; C08G 59/00; C08G 75/00
[52] U.S. Cl. ......................... 549/78; 528/86; 528/380
[58] Field of Search .......................... 549/78

[56] References Cited

U.S. PATENT DOCUMENTS 3,749,738  7/1973  Hatch.
3,862,079  1/1975  Pleuddemann.
4,049,849  9/1977  Brown ................................ 549/78

Primary Examiner—Alan Siegel

Attorney, Agent, or Firm—Charles J. Enright

[57] ABSTRACT

New, highly reactive, polymerizable compounds are described, corresponding to the formula

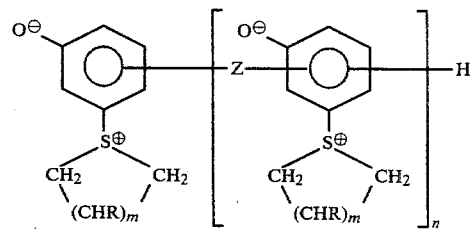

wherein R is H or lower alkyl, Z is a linking entity which is a chemical bond, lower alkylene, lower alkylenedioxy, O or the like, m is an integer 2–3 and n is 0–10. They are prepared by reaction of the corresponding 3(methylthio)phenolic compounds with the appropriate 1,4- or 1,5-alkylene bromide and converting the resulting cyclic sulfonium bromide to the zwitterion by treatment with a strong base anion-exchange resin in hydroxide form. They polymerize in a few minutes at 30°–50° C. to form polymers useful as coatings.

2 Claims, No Drawings

CYCLIC META-SULFONIUM-PHENOXIDE ZWITTERIONS

This is a continuation of application Ser. No. 892,049, filed Mar. 31, 1978 and now abandoned, which is a continuation of Ser. No. 582,554, filed on May 29, 1975, and now abandoned.

BACKGROUND OF THE INVENTION

The ortho and para isomers of the compounds of the present invention are known compounds and are known to be readily polymerizable (Hatch et al., U.S. Pat. Nos. 3,636,052 and 3,660,431).

SUMMARY OF THE INVENTION

The compounds of the invention (Formula IV) are made by converting the corresponding salts (II) to the free sulfonium base. Dehydration of the solution of the base then produces the zwitterion (III). The intermediates (II) are in turn made by reacting the corresponding meta-(methylthio)phenolic compound (I) with a 1,4 or 1,5-dibromoalkane. These reactions can be summarized as follows:

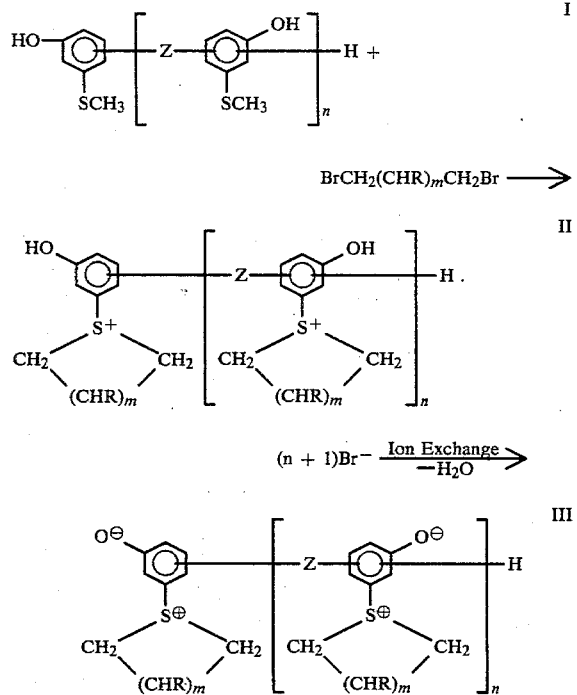

wherein each R is H or lower alkyl, Z is a linking entity which may be a chemical bond, lower alkylene, lower alkylenedioxy, O, S or the like, m is an integer 2-3 and n is 0 to about 10. It is to be understood that the aromatic rings in the above formulas may bear one or more inert substituents, such as lower alkyl groups. By "lower alkyl" and "lower alkylene" is meant radicals containing up to about 5 carbon atoms.

The invention includes the intermediates (II) as well as the zwitterions III and polymers thereof. The zwitterions are useful as polymerizable monomers. They readily polymerize at or slightly above room temperature to form polymers having mer groups of the formula

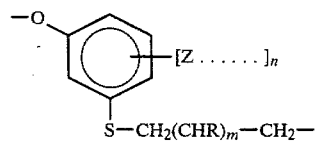

wherein the moieties attached through Z, if any, will also contain ring-opened units connected through sulfide linkages. When n is zero the polymers are linear whereas when n is 1 or more the polymers are crosslinked. The polymers are useful in surface coatings.

DETAILED DESCRIPTION OF THE INVENTION

A. Preparation of m-(Methylthio)phenols (I)

These intermediates are conveniently made from the appropriate bromo phenol by reaction with methyl disulfide in the presence of copper powder and a tertiary amine such as pyridine or lutidine:

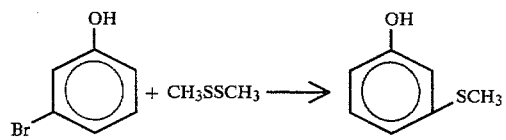

The aromatic ring of the phenol may bear inert substituents, such as lower alkyl, Cl, F, etc. In making polynuclear (methylthio)phenols, it is often desirable to first make the appropriate mononuclear (methylthio)phenol and then interconnect these links to make the desired chain; e.g.,

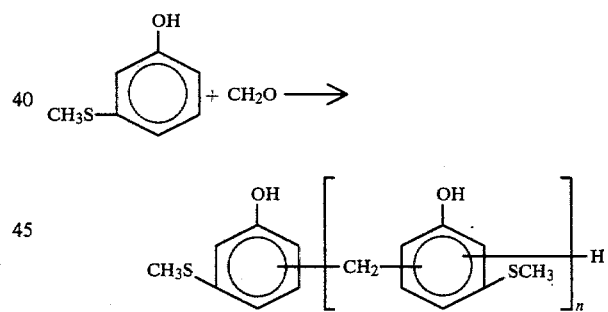

Alternatively the appropriate polyphenolic compound can be condensed with methyl disulfide as described above.

B. Preparation of Cyclic Sulfonium Salts (II)

The reaction of the (methylthio)phenols (I) with the 1,4- or 1,5-dibromoalkane is readily effected by heating the reactants at about 100°–150° C. under an inert atmosphere and with removal of the byproduct methyl bromide, substantially as reported by Hatch et al., U.S. Pat. No. 3,636,052 (Method 1C).

C. Conversion of Salts (II) into Zwitterions (III)

The free sulfonium hydroxides are very labile and spontaneously dehydrate at room temperature to form the zwitterions (III). For this reason they ordinarily exist only in solution. The salts are conveniently converted to the free base by reaction with a strong base ion exchange resin in hydroxide form, essentially as disclosed by Hatch et al. in U.S. Pat. Nos. 3,636,052 and 3,660,431. It is necessary, however, to operate at temperatures no higher than about 20° C. when concentrating the product solution and isolating the product because of the great ease with which the product polymerizes. If a suitable solvent, such as methanol, is used in the preparation, the zwitterion precipitates as it is formed and can be separated from the mother liquor by filtration or decantation.

The products (III) are crystalline solids which are so easily polymerized that it is usually best to make and use them in the form of aqueous solutions rather than in pure form. When applied to surfaces to be coated, such solutions dry to leave solid polymeric coatings, even when dried at temperatures as low as 30°-40° C. On most common substrates, such as wood, glass and metals, these coatings are strongly adherent and have good hardness and toughness. They have all the advantages of the zwitterions disclosed by Hatch et al. in the above-cited patents, and in addition have much greater ease of polymerization, thus enabling their use to produce coatings on heat-sensitive surfaces at temperatures of only 30°-40° C. and with polymerization times of only a few minutes.

Various additives, such as pigments, dyes, fillers, etc., may be incorporated into the solutions from which coatings are to be cast. It is notable that colloidal silica not only acts as a filler and reinforcing agent to give greatly improved hardness and scratch resistance but also acts in effect as a polymerization accelerator, thus shortening the time needed for polymerization.

The monomers (III) can be homopolymerized or copolymerized with other cyclic sulfonium zwitterions, such as those disclosed by Hatch et al. Because of their extreme reactivity, they markedly accelerate the polymerization of the less reactive ortho- and para-sulfonium zwitterions of the type disclosed by Hatch et al.

SPECIFIC EMBODIMENTS OF THE INVENTION

The following examples illustrate the practice of the invention.

EXAMPLE 1

1-(3-Hydroxyphenyl)tetrahydrothiophenium Hydroxide Inner Salt (Zwitterion)

(a) Preparation of 3(Methylthio)phenol (I, $n=0$)

3-Bromophenol (143 g.; 0.83 mole), methyl disulfide (48.6 g.; 1.28 mole), copper powder (65.5 g.; 1.03 mole), and technical grade 2,4-lutidine (743 ml.) were added and mixed in respective order into a flask equipped with a mechanical stirrer. A small exotherm was noticed. The reaction mixture was slowly brought to reflux under a blanket of dry nitrogen. Upon reaching reflux (159° C.), a light brown precipitate (cuprous methyl mercaptide) appeared, and the reaction mixture was kept well agitated by the mechanical stirrer. After 24 hours of refluxing, the reaction solution was cooled and added slowly to a stirred solution of conc. HCl (825 ml.) and crushed ice. The resulting mixture was stirred for one hour. The precipitate was filtered, extracted with ether (thrice), and the ether extracts washed thrice with 10 percent NaOH (500 ml.). The basic solution was then re-acidified with conc. HCl to a pH of 3, extracted with methylene chloride, dried over sodium sulfate, and placed in vacuo to give 99.25 g. of crude product. Upon distilling, approximately 84 g. of pure 3-methylthiophenol (b.p. 97°-99° C./0.5 mm.) was obtained.

(b) Preparation of 1-(3-Hydroxyphenyl)thiophenium Bromide (II, $n=0$)

A mixture of 3.3 g. (0.0236 moles) 3-methylthiophenol and 27.0 g. (0.125 moles) of 1,4-dibromobutane was heated under a slow nitrogen flow for 5 hrs. at 120° C. with evolution of methyl bromide. Cooling gave a crystalline mass which was washed thoroughly with acetone and dried to yield 5.6 g. (91.0 percent yield) (m.p. 103°-105° C.) of 1-(3-hydroxyphenyl)thiophenium bromide. Purification is facilitated by conversion to the perchlorate and recrystallization from aqueous methanol.

Analysis for $C_{10}H_{13}SOBr$. Calcd: C, 45.98; H, 4.02; S, 12.28; O, 6.13; Br, 30.60. Found: C, 46.14; H, 5.00; S, 12.40; O, 6.15; Br, 30.45.

(c) Preparation of Cyclic Zwitterionic Monomer (III, $n=0$)

About 50.0 ml. of a strong base anion-exchange resin in hydroxide form (Dowex 1-X8 resin) was washed with water, then methanol, and slurried with a methanolic solution of 4.0 g. of 3-hydroxphenylthiophenium bromide or perchlorate. Additional resin was added and slurried until the methanolic solution showed a steady pH (10.3). After filtering the slurry an appropriate amount of de-ionized water (15 ml.) was added to the methanolic filtrate and the solution concentrated under conditions (10°-15° C./20 mm.) where polymerization would not occur. When all of the methanol was removed, there remained a 27.65 percent aqueous solution of (III, $n=0$).

(d) Homopolymerization of Monomer (III)

Using a No. 46 Meyer rod, a film of a 27.65 percent aqueous solution of monomer (III) was drawn onto a Styron ® chip and cured at 40° C. in 4 minutes with a force of warm air to give an opaque hydrophobic coating (½ mil. thick). The same film was applied to a 1/32" steel panel and then cured (120° C./30 min.), thus producing a coating that had an impact resistance of 160 inch lbs. Using a Ubbelohde viscometer, the polymer showed a specific viscosity of 0.13 in chlorobenzene at 105° C. This viscosity is equivalent to a molecular weight of about 15,000.

Analysis for $C_{10}H_{12}OS$. Calcd: C, 66.63; H, 6.71; O, 8.88; S, 17.79. Found: C, 66.59; H, 6.67; O, 8.77; S, 17.97.

(e) Copolymerization of Monomer (III)

(a) Without Silica

Equal weight amounts of a 27.65 percent aqueous solution of monomer (III) and a 32.6 percent aqueous solution of monomer (V) were mixed and a film drawn (with a 46 Meyer rod) on a Styron ® chip. A force of warm air at 40° C. cured the film in 8-10 minutes to a hard, clear, hydrophobic coating (½ mil, thick). Application of the same film onto 1/32" steel panel and then cured (120° C./30 min.), produced a coating with a Knoop hardness number of 18.68 and an impact resistance of 160 inch lbs.

(b) With Silica

Equal weight amounts of the above aqueous solution of zwitterionic monomers and a 30 percent colloidal suspension of silica were mixed and a film drawn (with a 46 Meyer rod) on a Styron ® chip. A force of warm air at 40° C. cured the film in 4 minutes to a hard, clear, hydrophobic coating (½ mil. thick). Application of the same film onto a 1/32" steel panel and then cured (120° C./30 min.) produced a coating with a Knoop hardness number of 31.66 and an impact resistance of less than 160 inch lbs. but good scratch resistance.

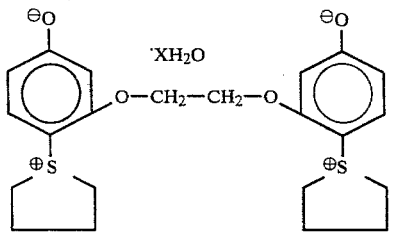

EXAMPLE 2

Preparation of Compound III wherein Z is $CH_2$, m is 2 and n is 2

(a) Preparation of (3-Methylthio)phenolic Novolac (I)

5.19 g (0.037 mole) of solid 3-methylthiophenol was dissolved in 12.5 ml of $CCl_4$. p-Toluenesulfonic acid (0.03 g) was dissolved into 1.5 g or 1.39 ml of 37 percent Formalin solution. Both solutions were added into an ampoule which was sealed and heated with stirring at 70° C. for 16 hours. After cooling, the ampoule was opened and the $CCl_4$ evaporated off using steam and a roto-vac. The resulting pink gum was dissolved in ether and washed with water to remove the p-toluenesulfonic acid catalyst and unreacted formaldehyde. After drying and evaporation of the ether solution, a pink gum remained. NMR spectroscopy ($^1H$) indicated that the product contained approximately 10 percent of unreacted m-methylthiophenol. The gum ($CH_3OH$ soluble) was not purified.

(b) Preparation of 3-Tetrahydrothiophenium Novolac Bromide (II)

2.45 g of the crude 3-methylthio-Novolac was mixed with 13.87 g. of 1,4-dibromobutane and heated under $N_2$ at 130° C. for 4 hours, during which time a white solid precipitated. After cooling, the white solid was collected, washed with water and methanol, and dried at 80° C. under vacuum for 4 hours. The washing with water and methanol removed the byproduct 3-hydroxyphenylthiophenium bromide. The resulting solid gave a positive test for ionic bromide with ethanolic silver nitrate solution. The product was soluble in dimethylformamide and dimethylsulfoxide. The characteristic methylthio group of the precursor was absent in the NMR spectrum of the product.

Average Molecular Wt.: (DMF solvent), 810, corresponding to n=2 in Formula II.

(c) Preparation of Zwitterionic Monomer (III)

1.0 g of 3-tetrahydrothiophenium Novolac bromide was suspended into 20.0 g of methanol followed by the addition of excess Dowex 1-X8 resin, hydroxide form. The suspension was stirred at R.T. for 30 min. or until a pH of 10.5 was obtained. During the stirring action most of the sulfonium salt dissolved, followed by the formation of a white precipitate. The resulting basic reaction mixture was filtered, yielding 0.15 g of a white solid. The colorless methanol filtrate gave a negative Beilstein test for halogen. The solids from the methanol solution were calculated to be about 5.0 wt. percent.

(d) Polymerization of the Zwitterionic Monomer (III)

A 5 percent methanol solution of monomer was applied as a thin film to a stainless steel panel and heated at 50° C. The film was examined periodically to determine the minimum time for the film to become hydrophobic. It was found that in approximately 5 minutes the film was hydrophobic. After post-curing the film at 50° C. for 15 minutes, a hard, clear, colorless polymer was produced which was not attacked by dimethylformamide, dimethyl sulfoxide nor methanol, indicating that the polymer was probably crosslinked.

Elemental Analysis of the crosslinked polymer: Found: C, 64.31; H, 6.15; S, 17.43; Br, 0.47.

We claim:

1. A compound of the formula:

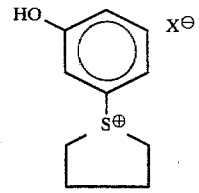

wherein $X^\ominus$ is one equivalent of a compatible anion and the aromatic ring may bear lower alkyl substituents.

2. A compound of the formula:

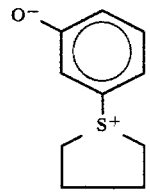

wherein the aromatic ring may bear lower alkyl substituents.

* * * * *